USOO8389481B2

(12) United States Patent
Barton et al.

(10) Patent No.: US 8,389,481 B2
(45) Date of Patent: Mar. 5, 2013

(54) GLUTAMATE-ENHANCED CELL-PENETRATING PEPTIDES AND METHODS OF USING SAME

(75) Inventors: Beverly E. Barton, West Orange, NJ (US); H. Dan Lewis, Orange, NJ (US); Robert J. Donnelly, Fords, NJ (US); Ali Husain, Voorhees, NJ (US); Dimitrios Barlos, Newark, NJ (US); Sheraz Riaz, Nutley, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 410 days.

(21) Appl. No.: 12/617,525

(22) Filed: Nov. 12, 2009

(65) Prior Publication Data

US 2010/0137187 A1    Jun. 3, 2010

Related U.S. Application Data

(60) Provisional application No. 61/199,117, filed on Nov. 12, 2008.

(51) Int. Cl.
  *A61K 38/10*   (2006.01)
  *A61K 38/04*   (2006.01)
  *C12N 5/00*    (2006.01)
  *C12N 5/02*    (2006.01)
  *C07K 5/00*    (2006.01)
  *C07K 7/00*    (2006.01)
  *C07K 16/00*   (2006.01)
  *C07K 17/00*   (2006.01)
(52) U.S. Cl. .................. 514/21.5; 435/375; 530/327
(58) Field of Classification Search .................. None
  See application file for complete search history.

(56) References Cited

PUBLICATIONS

Ramachandra et al. Embryonic development in the primitive bilaterian *Neochildia fusca*: normal morphogenesis and isolation of POU genes Brn-1 and Brn-3. Dev Genes Evol. 2002. vol. 212, pp. 55-69.*
Barton et al., Novel Single-Stranded Oligonucleotides that Inhibit STAT3 Induce Apoptosis In Vitro and In Vivo in Prostate Cancer Cell Lines, Mol. Cancer Ther. 2004, 3(10):1183-1191.
Lewis et al., STAT3 Inhibition in Prostate and Pancreatic Cancer Lines by STAT3 Binding Sequence Oligonucleotides: Differential Activity Between 5' and 3' Ends, Mol. Cancer Ther. 2008, 7(6): 1543-1550.
Leach, Targeting prostate-specific membrane antigen in cancer therapy: can molecular medicine be brought to the surface? Cancer Biol. Ther. 2004, 3(6): 559-560.
Mhaka et al., Use of methotrexate-based peptide substrates to characterize the substrate specificity of prostate-specific membrane antigen (PSMA), Cancer Biol. Ther. 2004, 3(6): 551-558.
El-Andaloussi et al., TO10, a delivery vector for decoy oligonucleotides targeting the Myc protein, J. Control Release 2005, 110(1): 189-201.
Heckl et al., Intracellular visualization of prostate cancer using magnetic resonance imaging, Cancer Res. 2003, 63(16): 4766-4772.
Ragin et al., Cellular Import Mediated by Nuclear Localization Signal Peptide Sequences, Chemistry & Biology 2002, 9(8): 943.
Bendifallah et al., Evaluation of Cell-Penetrating Peptides (CPPs) as Vehicles for Intracellular Delivery of Antisense Peptide Nucleic Acid (PNA), Bioconjugate Chem. 2006, 17(3): 750-758.
Fretz et al., Temperature-, concentration-, and cholesterol-dependent translocation of L- and D-octa-arginine across the plasma and nuclear membrane of CD34+ leukemia cells, Biochem. J. 2007, 403(2): 335-342.
Mann and Frankel, Endocytosis and targeting of exogenous HIV-1 Tat protein, EMBO J. 1991, 10(7): 1733-1739.
Thoren et al., Uptake and analogs of penetratin, Tat(48-60) and oligoarginine in live cells, Biochemical and biophysical Research Communications 2003, 307(1): 100-107.
Richard et al., Cell-penetrating peptides. A reevaluation of the mechanism of cellular uptake, J. Biol. Chem. 2003, 278(1): 585-590.
Foley et al., Culture conditions influence uptake and intracellular localization of the membrane permeable cGMP-dependent protein kinase inhibitor DT-2, Frontiers Bioscience 2005, 10:1302-1312.
Koppelhus and Nielsen, Cellular delivery of peptide nucleic acid (PNA), Adv. Drug Deliery Rev. 2003, 55: 267-280.
Aggaral et al., A dimeric peptide that binds selectively to prostate-specific membrane antigen and inhibits its enzymatic activity, Cancer Res. 2006, 66(18): 9171-9177.
Liu et al., Prostate-specific membrane antigen directed selective thrombotic infarction of tumors, Cancer Res. 2002, 62(19): 5470-5475.
Ghosh and Heston, Tumor target prostate specific membrane antigen (PSMA) and its regulation in prostate cancer, Journal of Cellular Biochemistry 2004, 91(3): 528-539.
Chang et al., Metabotropic Glutamate Receptor 4 Expression in Colorectal Carcinoma and Its Prognostic Significance, Clin. Cancer Res. 2005, 11(9): 3288-3295.
Shin et al., Metabotropic glutamate receptors (mGlus) and cellular transformation, Neuropharmacology 2008, 55(4): 396-402.
Ippolito et al., Linkage between cellular communications, energy utilization, and proliferation in metastatic neuroendocrine cancers, Proc. Natl. Acad. Sci. U.S.A. 2006, 103(33): 12505-12510.

* cited by examiner

*Primary Examiner* — Marcela M Cordero Garcia
(74) *Attorney, Agent, or Firm* — Lowenstein Sandler LLP (57) ABSTRACT

Disclosed herein are novel glutamate-enhanced cell-penetrating peptides (CPPs) for use as delivery vehicles to mediate intracellular uptake of therapeutic payloads and methods of using the same.

13 Claims, 6 Drawing Sheets

Figure 3A merge

DRAQ5

FITC

```
                        SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Synthetically produced Glu peptide
      (Peptide 351)

<400> SEQUENCE: 1

Glu Glu Glu Ala Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetically produced Glu peptide (Peptide
      352)

<400> SEQUENCE: 2

Glu Glu Glu Ala Ala Lys Lys Lys
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetically produced Glu-Oct6 peptide
      (Peptide 353)

<400> SEQUENCE: 3

Glu Glu Glu Ala Ala Gly Arg Lys Arg Lys Lys Arg Thr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetically produced Oct6 peptide (Peptide
      356)

<400> SEQUENCE: 4

Gly Arg Lys Arg Lys Lys Arg Thr
1               5

<210> SEQ ID NO 5
<211> LENGTH: 13
<212> TYPE: PRT
<213> ORGANISM: Artificial Sequence
<220> FEATURE:
<223> OTHER INFORMATION: Synthetically produced Phe-Oct6 peptide
```

```
(Peptide 361)

<400> SEQUENCE: 5

Phe Phe Phe Ala Ala Gly Arg Lys Arg Lys Lys Arg Thr
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetically produced Asn-Oct6 peptide
      (Peptide 362)

<400> SEQUENCE: 6

Asn Asn Asn Ala Ala Gly Arg Lys Arg Lys Lys Arg Thr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetically produced Phe-Oct6 peptide
      (Peptide 365)

<400> SEQUENCE: 7

Phe Phe Phe Ala Ala Gly Arg Lys Arg Lys Lys Arg Thr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetically produced Asn-Oct6 peptide
      (Peptide 366)

<400> SEQUENCE: 8

Asn Asn Asn Ala Ala Gly Arg Lys Arg Lys Lys Arg Thr
1               5                   10

<210> SEQ ID NO 9
<211> LENGTH: 15
<212> TYPE: DNA
<213> ORGANISM: Artificial Sequence
<220> FEATURE:
<223> OTHER INFORMATION: Synthetically produced carboxyfluorescein
      peptide nucleic acid

<400> SEQUENCE: 9
tatgatctcc tccgt                                                    15
```

GLUTAMATE-ENHANCED CELL-PENETRATING PEPTIDES AND METHODS OF USING SAME

CLAIM OF PRIORITY

This application claims priority to U.S. provisional application No. 61/199,117, filed Nov. 12, 2008, the disclosure of which is hereby incorporated by reference in its entirety.

STATEMENT OF FEDERAL FUNDING

The invention was made with U.S. government support, and the U.S. Government may have certain rights in the invention, as provided for by the terms of Grant ID Number CA121782 awarded by the National Institute of Health on Feb. 23, 2007.

STATEMENT UNDER 37 C.F.R. §1.821(f)

In accordance with 37 C.F.R. §1.821(f), the content of the attached Sequence Listing and the attached computer readable copy of the Sequence Listing are identical.

BACKGROUND OF THE INVENTION

Experimental therapeutic approaches for androgen-resistant prostate cancer are actively investigated. It is known that modified oligonucleotides bearing STAT3 binding sequences induced apoptosis in DU-145 and other androgen-insensitive prostate cancer cell lines and retarded the in vivo growth of DU-145 cells in a xenograft model. Such inhibitors are attractive in theory but lack a practical method for delivery in the clinical setting. One possible approach to overcome this roadblock is to use peptide-mediated transport, thereby coupling a cell-penetrating peptide (CPP) to an anti-STAT3 therapeutic payload. An inherent advantage of using CPPs is the ability to design cell specificity in the sequence, as well as target organelle specificity through inclusion of nuclear localization signals (NLS).

CPPs for prostate cancer have been examined in conjunction with delivery of therapeutic payloads including methotrexate-loaded liposomes, double-stranded decoys, and radioactive gadolinium complexes targeted to c-myc. The NLS of several transcription factors were compared in various tumor types with varying degrees of efficacy with regard to uptake and nuclear localization. As for delivery of an oligonucleotide payload, one study using CPPs consisting of cell surface ligands linked to NLS and conjugated to peptide nucleic acids (PNAs) found optimal efficacy under serum-free conditions at 5 mM, a concentration that is not commercially feasible due to prohibitive costs. Clearly, more studies on optimizing CPPs for delivery of therapeutic oligonucleotide or PNA payloads are needed in order to bring new therapeutic entities to the clinic.

SUMMARY OF THE INVENTION

This invention relates to new cell-penetrating peptides designed for maximal uptake by prostate cancer cells and to the use of the peptides in the treatment of cancer. Recent papers on peptide uptake indicate that nuclear colocalization, even by transcription factor NLS, is not easily achieved. Thus the description herein of the enhancement of uptake and nuclear localization of a NLS through addition of a peptide is a new advance in the art.

It is an object of the invention to provide a cell-penetrating peptide comprising a glutamate peptide bound to a NLS peptide by a linker In certain embodiments, the linker is a peptide. In further embodiments, the linker comprises alanine, glycine, or a combination thereof. In certain embodiments, the the glutamate peptide is bound to the N-terminus of the NLS peptide. In other embodiments, the cell-penetrating peptide further comprises a FITC label.

In certain embodiments, the NLS peptide is derived from a transcription factor. In further embodiments, the transcription factor is Oct6.

It is a further object of the invention to provide a cell-penetrating further comprising a therapeutic payload. In certain embodiments, the therapeutic payload is bound to the C-terminus of the NLS peptide. In further embodiments, the therapeutic payload comprises a nucleic acid, a liposome, a diagnostic molecule, or a combination thereof In other embodiments, the therapeutic payload comprises a STAT3-inhibiting oligonucleotide, carboxyfluorescein peptide nucleic acid, SEQ ID NO: 9, or a combination thereof. In some embodiments, the therapeutic payload inhibits the growth of a cell. In certain embodiments, the therapeutic payload inhibits the growth of a cancer cell. In further embodiments, the therapeutic payload inhibits the growth of prostate, breast, or pancreatic cancer cells.

It is a further object of this invention to provide a cell-penetrating peptide that is capable of localizing in the nucleus of a cell when incubated with said cell. In some embodiments, the cell-penetrating peptide is capable of localizing in the nucleus of a cancer cell. In further embodiments, the cell-penetrating peptide is capable of localizing in the nucleus of a prostate, breast, or pancreatic cancer cell.

It is a further object of this invention to provide a cell-penetrating peptide comprising the sequence of SEQ ID NO: 3, that is, EEEAAGRKRKKRT.

It is a further object of this invention to provide a method of inducing apoptosis in a cell comprising incubating a colony of cells with a cell-penetrating peptide comprising a glutamate peptide bound to a NLS peptide by a linker. In certain embodiments, the incubation step is carried out at a temperature between 20° C. and 37° C., inclusive. In further embodiments, the incubation step is carried out at a temperature of at least 37° C. In certain embodiments, the incubation step is carried out for between 1 and 4 hours, inclusive. In other embodiments, the incubation step is carried out for least 4 hours. In some embodiments, the incubation step is carried out in vitro. In other embodiments, the incubation step is carried out in vivo.

In certain embodiments, the method employs a linker that is a peptide. In further embodiments, the method employs a linker that comprises alanine, glycine, or a combination thereof. In certain embodiments, the method employs a glutamate peptide that is bound to the N-terminus of the NLS peptide. In other embodiments, the method employs cell-penetrating peptide further comprising a FITC label.

In certain embodiments, the method employs a NLS peptide that is derived from a transcription factor. In further embodiments, the method employs a NLS derived from the transcription factor Oct6.

It is a further object of the invention to provide a method of inducing apoptosis in a cell comprising incubating a colony of cells with a cell-penetrating peptide further comprising a therapeutic payload. In certain embodiments, the method employs a therapeutic payload that is bound to the C-terminus of the NLS peptide. In further embodiments, the method employs a therapeutic payload comprising a nucleic acid, a liposome, a diagnostic molecule, or a combination thereof. In other embodiments, the method employs a therapeutic payload comprising a STAT3-inhibiting oligonucleotide, carboxyfluorescein peptide nucleic acid, SEQ ID NO: 9, that is, TATGATCTCCTCCGT, or a combination thereof. In some embodiments, the method employs a therapeutic payload that inhibits the growth of a cell. In certain embodiments, the method employs a therapeutic payload that inhibits the growth of a cancer cell. In further embodiments, the method employs a therapeutic payload that inhibits the growth of prostate, breast, or pancreatic cancer cells.

It is a further object of this invention to provide a method of inducing apoptosis in a cell employing a cell-penetrating peptide that is capable of localizing in the nucleus of a cell when incubated with said cell. In some embodiments, the method employs a cell-penetrating peptide that is capable of localizing in the nucleus of a cancer cell. In further embodiments, the method employs a cell-penetrating peptide that is capable of localizing in the nucleus of a prostate, breast, or pancreatic cancer cell.

It is a further object of this invention to provide a method of inducing apoptosis in a cell employing a cell-penetrating peptide comprising the sequence of SEQ ID NO: 3, that is, EEEAAGRKRKKRT.

It is a further object of this invention to provide a method of inhibiting the uptake of a cell-penetrating peptide in a colony of cells, comprising culturing the cells with NaN$_3$.

It is a further object of this invention to provide a cell-penetrating peptide comprising a glutamate peptide bound to an Oct6 NLS peptide by an alanine linker.

It is a further object of this invention to provide a hybrid molecule comprising a glutamate peptide bound to an Oct6 NLS peptide by an alanine linker and a therapeutic payload.

It is a further object of this invention to provide a composition comprising a cell-penetrating peptide and a STAT3-inhibiting therapeutic payload.

It is a further object of this invention to provide a method of treating cancer comprising administering a cell-penetrating peptide as described herein to a patient in need thereof.

It is a further object of this invention to provide a method of treating cancer comprising administering a hybrid molecule comprising a glutamate peptide bound to an Oct6 NLS peptide by an alanine linker and a therapeutic payload to a patient in need thereof.

It is a further object of this invention to provide a method of treating cancer comprising administering a composition comprising a cell-penetrating peptide and a STAT3-inhibiting therapeutic payload to a patient in need thereof.

For the purposes of this application, therapeutic payload means an agent that can provide a therapeutic and/or diagnostic effect, and includes, e.g., drugs, therapeutic compounds, radioactive compounds, chemotherapy agents, DNA or RNA, proteins, liposomes, diagnostic dyes, small molecules, MRI contrast agents, and combinations thereof.

BRIEF DESCRIPTION OF THE DRAWINGS

The invention is more fully described below in conjunction with the Figures wherein:

FIG. 1 shows peptide uptake by prostate cancer cell lines.

FIG. 3D merged image shows the phase contrast image overlayed on the fluorescence images.

DETAILED DESCRIPTION OF THE INVENTION

This invention relates to new CPPs designed for maximal uptake by prostate cancer cells. By adding a glutamate peptide to the N-terminus of the Oct6 NLS via a linker peptide, a novel CPP was created that entered LNCaP and DU-145 cells readily. As little as 30 nM of FITC-labeled peptide was sufficient to stain 60-70% of the cells. Addition of a simple peptide, KKK, enhanced uptake 10-fold and addition of the NLS of the transcription factor Oct6 enhanced uptake 100-fold. Moreover, combining the glutamate peptide plus an alanine linker to the Oct6 NLS created a novel peptide with better nuclear localization properties than either the glutamate or Oct6 peptides alone. Finally, when the novel peptide was coupled to a carboxyfluorescein PNA, uptake by DU-145 cells was observed. It was concluded that rational design of CPPs for enhanced cancer cell-specific uptake can be useful for delivery of therapeutic payloads into the nuclei of targeted cells.

The use of NLS peptides was explored because of their potential to ferry therapeutic payload cargoes efficiently. Previously, it was observed that the Oct6 NLS peptide accumulated in the endosomal compartments of cells. However, here it was observed that addition of peptide EEEAA (SEQ. ID NO. 1) to the N-terminus of the Oct6 NLS enhanced cellular uptake and also enhanced nuclear localization. It was further observed that although peptide 353 facilitated entry of a PNA into DU-145 cells, it required concentrations above 300 nM and longer incubation times than unconjugated peptide 353. It was hypothesized that there is a large energy barrier to overcome for efficient transport of PNA into cells, despite their neutral charge and despite the apparently enhanced uptake properties of the CPP peptide 353. It is entirely possible that peptide 353 would function as a more efficient CPP if the form of the therapeutic payload was changed from a PNA to a different entity, such as a locked nucleic acid. Notwithstanding, peptide 353 has exhibited high potential as a probe for studying nuclear localization events, and as a CPP for ferrying other forms of therapeutic payloads, such as peptides or liposomes.

Glutamate receptors are known to be overexpressed by cancer cells. In prostate cancer, the best known is PSMA, which binds carboxy glutamates. PSMA is not involved because DU-145 cells are PSMA-negative, and because the glutamate is on N-termini of the peptides. Metabotropic glutamate receptors are usually found on neuronal cells but are found to be aberrantly expressed by malignant cells. These glutamate receptors mediated 5-fluorouracil resistance in human colon cancer cells. Glutamate receptors are implicated in transformation to malignancy; it's hypothesized that glutamate receptors overexpression may be a common feature of tumor pathogenesis. The activity of normal glutamate receptors in ectopic cellular environments may involve signaling pathways, which dysregulate cell growth, ultimately leading to tumorigenesis. Thus, dysregulated and aberrantly-expressed glutamate receptors may function as oncogenes. Malignant prostatic neuroendocrine cells proliferate more when glutamate receptors are stimulated; they use glutamate as a substrate for NADH biosynthesis, producing increased levels of free fatty acids. These activities correlate with the aggressive nature of these tumors. Glutamate receptors have been understudied and certainly have not yet been widely used for cancer-specific targeting. Since glutamate receptors are overexpressed on a variety of solid tumors, they should lend themselves rather well to cancer cell targeting by a variety of strategies, including CPP design.

EXAMPLES

Summary of Findings.

The use of the Oct6 NLS peptide as a CPP was explored. Peptide 353 was shown to gain entry into DU-145 and LNCaP cells quickly and efficiently, and localized to the nucleus. Its ability to function as a CPP was concentration- and temperature-dependent, and abrogated in the presence of azide. The homologous peptide 356, which was comprised of the Oct6 NLS peptide alone and lacked the N-terminal glutamate residues, did not localize to the nucleus. The ability of peptide 353 to function as a CPP was lost when Phe or Asn were substituted for the Glu residues on peptide 353. Finally, peptide 353 facilitated entry of a carboxylysyl-fluorescein PNA into DU-145 cells, albeit at reduced efficiency that peptide 353 alone.

Addition of Peptide EEEAA (SEQ. ID NO. 1) to the Oct6 NLS Enhanced its Uptake.

Carboxyfluorescein and carboxydansyl peptides were synthesized by FMoc solid phase chemistry and purified by high performance liquid chromatography (HPLC). Sequences were verified by HPLC. Purified peptides were dissolved in buffer before addition to cultures of cells. The peptides used are listed in Table 1; synthesis numbers are used for reference in the text. The purpose of the alanine residues in some peptides was to serve as a linker peptide between two putative functional peptides, the glutamate peptide and the NLS peptide.

TABLE 1

Novel Peptides and Peptide-PNAs Included in Studies

| Synthesis # | Description | Sequence | Molecular Weight |
|---|---|---|---|
| 350 | Glu peptide 1 | EEE-FITC | 776 Da |
| 351 | Glu peptide 2 | EEEAA-FITC (SEQ ID NO: 1) | 919 Da |
| 352 | Glu peptide 3 | EEEAAKKK-FITC (SEQ ID NO: 2) | 1303 Da |
| 353 | Glu-Oct6 | EEEAAGRKRKKRT-FITC (SEQ ID NO: 3) | 1930 Da |
| 356 | Oct6 | GRKRKKRT-FITC (SEQ ID NO: 4) | 1400 Da |
| 361 | Phe-Oct6-FITC | FFFAAGRKRKKRT-FITC (SEQ ID NO: 5) | 1984 Da |
| 362 | Asn-Oct6-FITC | NNNAAGRKRKKRT-FITC (SEQ ID NO: 6) | 1885 Da |
| 365 | Phe-Oct6-dansyl | FFFAAGRKRKKRT-K-dansyl (SEQ ID NO: 7) | 1875 Da |

TABLE 1-continued

Novel Peptides and Peptide-PNAs Included in Studies

| 366 | Asn-Oct6-dansyl | NNNAAGRKRKKRT-K-dansyl (SEQ ID NO: 8) | 2058 Da |

| Description | Sequence |
|---|---|
| 353-PNA | EEEAAGRKRKKRT-TATGATCTCCTCCGT-K-FITC (SEQ ID NO: 9) |

Legend: Carboxyfluorescein and carboxydansyl peptides were synthesized by FMoc chemistry at the Molecular Resources Facility, UMDNJ. They were purified by HPLC and sequence verified by the same technique. Carboxydansyl peptides are synthesized using lysyl dansyl moieties. The peptide-PNA 353-PNA was synthesized by BioSynthesis; it was purified by HPLC and verified by MALDI-TOF. The letters in bold indicate the PNA portion of the molecule. The FITC moiety was coupled to the PNA as a lysyl-FITC, due to the requirements of PNA chemistry.
Note: the SEQ. ID NOs. provided are drawn to the peptide portion of the compound only.

Uptake of peptides by live cells was compared by flow cytometry, using the exclusion dye 7-amino actinomycin D (7-AAD) to exclude dead cells from analyses.

Figure 1A:
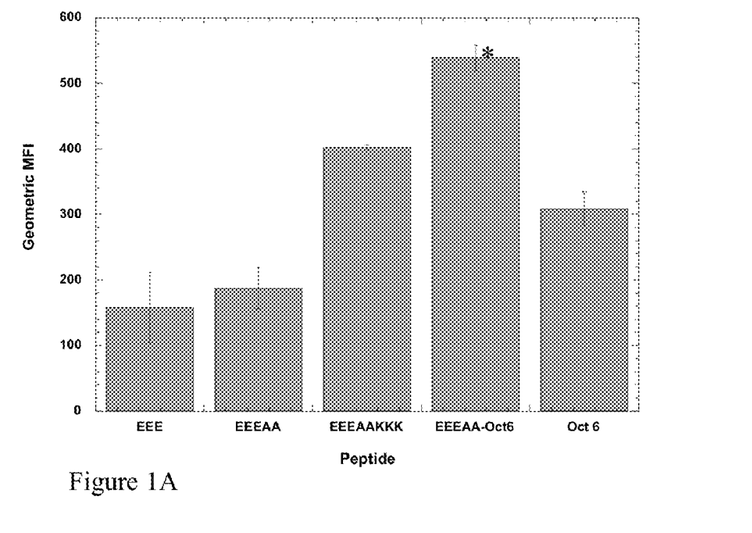
FIG. 1A: Enhancement of Oct6 uptake by EEEAA (SEQ ID NO: 1). DU-145 cells were incubated with 500 nM peptides for 4 hours in Materials and Methods. Harvested washed cells were subjected to flow cytometry on a FACScan. Dead cells were excluded by gating on 7-AAD-negative cells. *=geometric MFI of peptide 352 or 353 was significantly greater than peptide 350 ($p<0.01$) or 356 ($p<0.05$) by paired ANOVA. The average of 2 replicate experiments is shown.
Figure 1B:
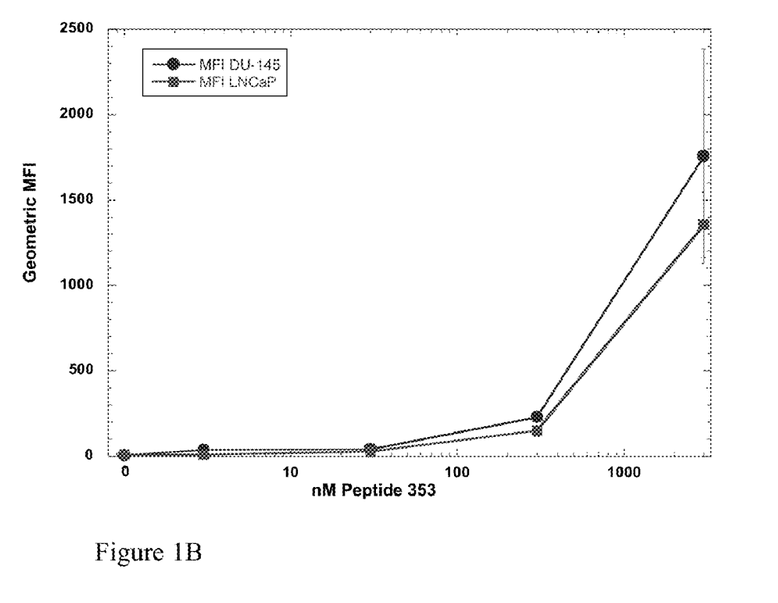
FIG. 1B: Effect of concentration on uptake of peptide 353 by DU-145 and LNCaP cells. Concentration of peptide 353 ranging from 0 to 3000 nM were incubated with DU-145 or LNCaP cells for 1 hr, at which time cells were harvested, washed, and processed for flow cytometry.

Because logarithmic amplification of fluorescence detectors were employed, the geometric MFIs were compared between samples. In comparing the geometric MFI among the peptides, it was noted that peptides 350 and 351 exhibited the lowest values, whereas addition of either KKK or the Oct6 NLS (peptides 352 and 353) significantly increased the geometric MFIs after 4 hrs incubation. Thus it appears that inclusion of even a minimal NLS such as KKK profoundly influenced cellular uptake. The influence of the Oct6 NLS on uptake was even more dramatic; however, uptake of the Oct6 NLS alone (that is, peptide 356) was not nearly as great as that of peptide 353, leading us to hypothesize that both parts of the peptide, EEEAA (SEQ ID NO: 1) and the Oct6 NLS, contribute to the enhanced property of peptide 353 to function as a CPP. The kinetics of uptake for peptide 353 were found to be rapid, although saturation was not reached. FIG. 1B shows that in both DU-145 and LNCaP cells, the geometric MFI of 500 nM at 1 hr extrapolated from the graph is nearly the same as that measured at 4 hr (FIG. 1A). In the presence of 3 µM, the geometric MFIs of the two cell lines was 1500-2000, and uptake was still linear. Inclusion of higher concentrations of peptide was not feasible, due to the limited amount of peptide. Substitution of Phe or Asn for Glu Abrogated Peptide Uptake.

Figure 1C:
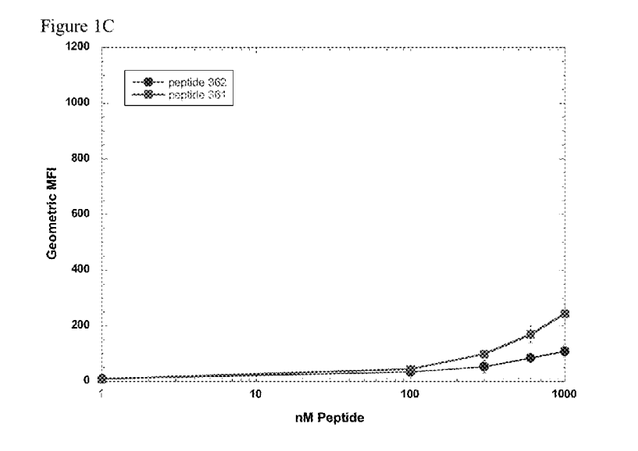
FIG. 1C: Effect of substituting Phe or Asn for Glu on peptide uptake by DU-145 cells. DU-145 cells were incubated with 0 to 1000 nM of carboxyfluorescein-labeled peptides 361 and 362 for 1 hr. at 37° C. Cells were then harvested, washed, counterstained with 7-AAD, and analyzed by flow cytometry to quantify fluorescence. At 3000 nM, viability of DU-145 cells fell below 50%; therefore those data are not included in the graph. The average 3 independent experiments ±SD is shown.
Figure 1D:
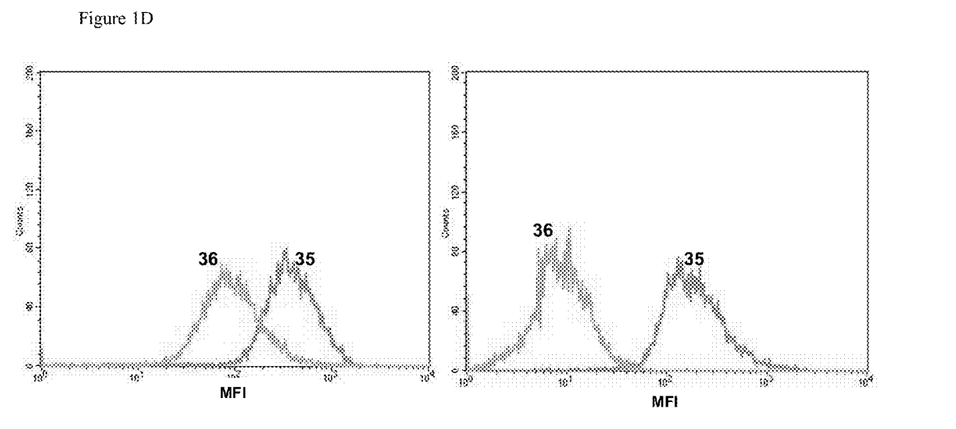
FIG. 1D: Effect of peptides 365 or 366 on uptake of peptide 353 by DU-145 cells. 300 nM of either dansyl-labeled peptide 361 or 362 were incubated with 300 nM fluorescein-labledpeptide 353 for 1 hr, at which time cells were harvested, washed, and analyzed on a BD LSR II for dansyl and FITC fluorescence. CellQuest Pro was used to analyze the fluorescence data. The line labeled 365 indicates dansyl fluorescence intensity; the line labeled 353 indicates fluorescein fluorescence intensity.

In order to determine if uptake of peptide 353 was receptor-mediated or receptor-specific in any way, Glu residues were substituted by Phe residues (peptide 361) or Asn residues (peptide 362). The resulting peptides were incubated at 0 to 3000 nM with DU-145 cells for 1 hr. Cells were then harvested and processed for analysis by flow cytometry. FIG. 1C shows that there was very little uptake of either peptide up to 300 nM (geometric MFI increased from approximately 40 to 100; the increase was not significant by paired ANOVA). At 3000 nM, peptides 361 and 362 induced cell death in more than 70% of the cells (determined by staining with 7-AAD); in the case of peptide 361, over 95% of DU-145 cells were positive for 7-AAD; therefore only geometric MFI for concentrations up to 1000 nM are shown in the figure. Coincubation of carboxyfluorescein peptide 353 with either carboxydansyl peptides 365 or 366 resulted in nearly unaltered uptake of peptide 353 without concomitant uptake of either 365 or 366 (FIG. 1D). It was noted that peptide 361 (Phe substituted for Glu) resulted in significant cell death at concentrations higher than 300 nM, a phenomenon not seen with peptide 362 or 353; thus concentrations of 361 or 362 higher than 300 nM were not examined in the competition experiments. The higher MFI observed for peptide 365 is likely due to the hydrophobicity of both the Phe residues and the dansyl fluorochrome. It was concluded from these experiments that peptide 353 bound to a cell-surface receptor through the glutamate residues.

Uptake of All Peptides was Temperature-Dependent, but Uptake of Peptides Containing the Oct6 NLS was Inhibited by $NaN_3$.

Figure 2:
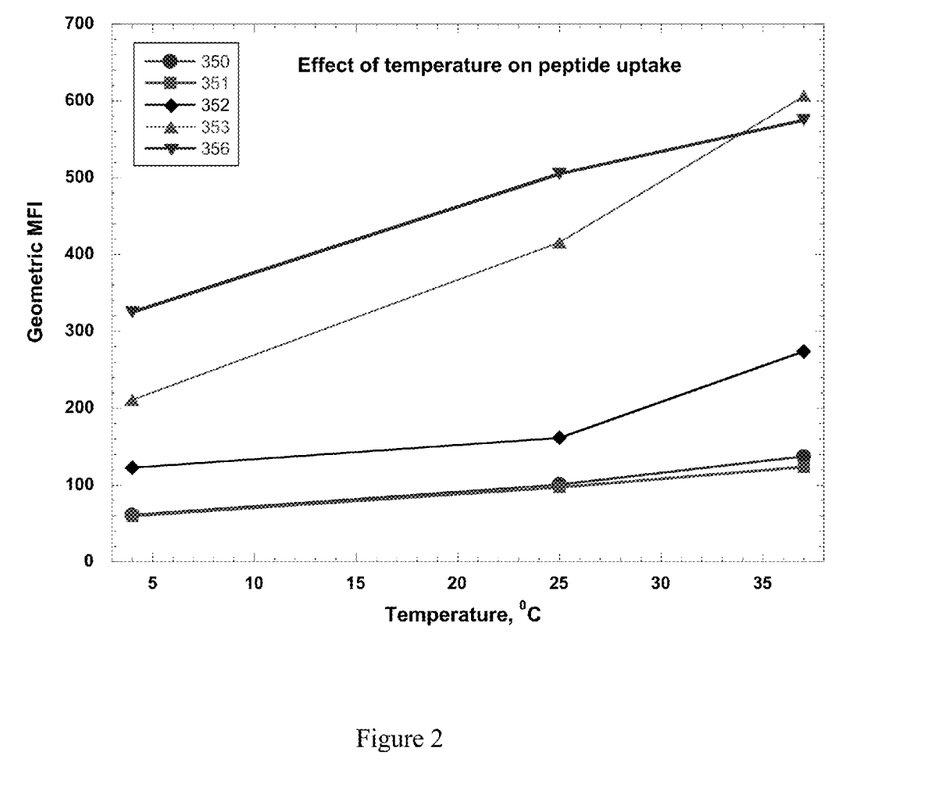
FIG. 2 shows effect of temperature on peptide uptake. Carboxyfluorescein-labeled peptides were incubated with DU-145 cells at 300 nM over 4 hours at 4, 25, and 37° C. Harvested washed cells were analyzed on a flow cytometer. The results of a representative experiment are shown.
Figures 3, 3A:
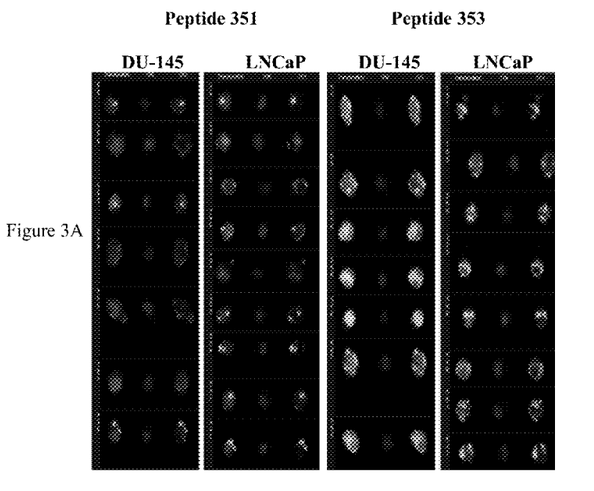
FIG. 3 shows imaging studies.
FIG. 3A: DU-145 and LNCaP cells were incubated with 250 nM peptides 351 or 353 for 4 hours, counterstained with 5 µM DRAQ 5, then fixed in paraformaldehyde and analyzed by imaging flow cytometry on an Amnis Imaging Cytometer. IDEAS software (Amnis) was used to generate and colorize the images. For each cell type and peptide, the left-most column shows the merged images, the middle column shows the DRAQ5 images, and the right-most column shows the FITC images. Analysis using IDEAS software revealed that peptide 353 distributed about 50% in nuclei and 50% in cytoplasm of cells, whereas only ~10% of nuclei were positive for DRAQ5 and FITC colocalization in the case of peptide 351.
Figures 3, 3B:
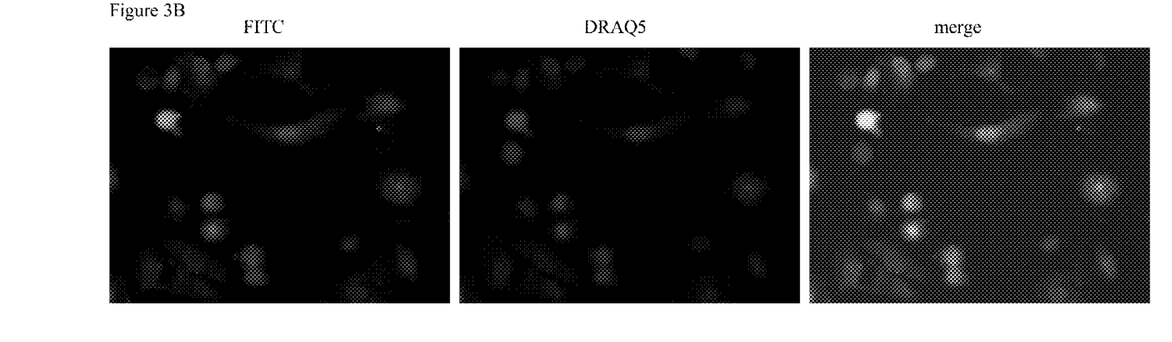
FIG. 3B: Live cell imaging of peptide 353 by DU-145 cells. 500 nM peptide 353 was incubated with DU-145 cells overnight (necessary for imaging purposes). Cells were washed with phenol red-free buffer, counter-stained with DRAQ5 at 10 µM, then examined under a Zeiss Axiovert 200 inverted phase contrast microscope with epifluorescence. The merged image confirms the presence of peptide 353 in nuclei.
Figures 3, 3C:
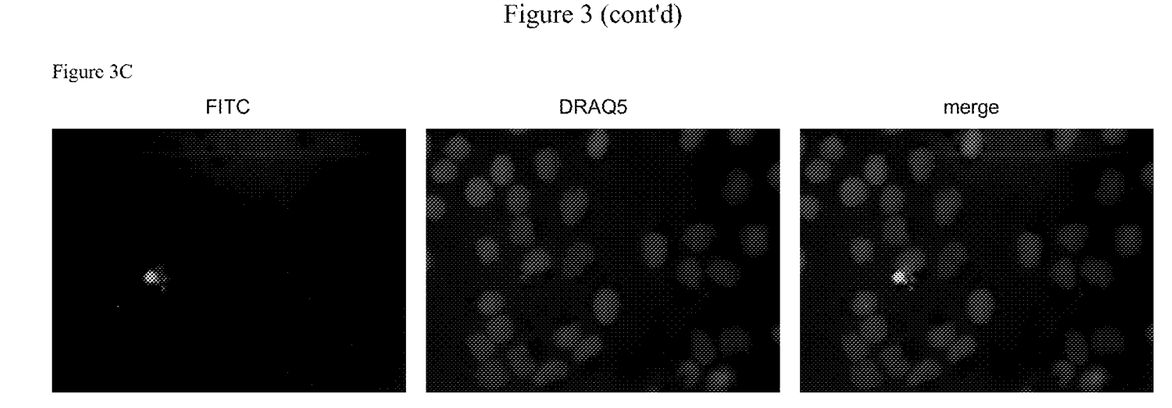
FIGS. 3C and D: DU-145 cells incubated with peptides 350 and 356, as described for FIG. 3B. Note the absence of FITC fluorescence in nuclei.

In order to determine if peptides entered cells by diffusion or by an ATP-dependent process, the following experiments were performed. First, uptake of 300 nM peptides was compared at 4, 23, and 37° C. for 4 hours. As shown in FIG. 2, uptake of all peptides was temperature-dependent, with best uptake observed at 37° C. Even at 4° C., peptides 353 and 356 exhibited greatly enhanced uptake, compared with the other peptides (average geometric MFI=486 for peptide 353 and geometric MFI=325 for peptide 356, compared with average geometric MFI=186 for peptide 352 and geometric MFI<100 for peptides 351 and 350). Temperature-dependence of peptide uptake has been found to correlate as well with segregation to intracellular compartments. Fretz and coworkers observed that at lower temperatures (4 to 12° C.), L- and D-octa-arginine peptides partitioned across nuclear and cytoplasmic compartments equally, moving to the endosomes of $CD34^+$ leukemia cells when ambient temperature rose to 30° C. and higher. They further observed that raising concentration affected which intracellular compartments were labeled by peptides. Similarly, temperature-dependent uptake of peptide 353 was observed (FIG. 2); furthermore peptide 353 partitioned across nuclei and cytoplasm (FIGS. 3A and B), whereas neither peptides 350 nor 356 exhibited appreciable nuclear localization (FIGS. 3C and D).

Usually, marked temperature dependence such as observed for these peptides is indicative of uptake by endoctytosis. If this is the case, then uptake would be expected to be inhibited by depletion of ATP. To investigate this, experiments were performed for 4 hr at 37° C. in the presence of $NaN_3$. Table 2 shows that the addition of 0.1 or 1% $NaN_3$ to cells had no effect on the uptake of peptides 350, 351, and 352 at 300 nM.

TABLE 2

Sodium Azide Inhibited Uptake of Peptides with Oct6 NLS

| Peptide | NaN3, % | Geometric MFI | % Inhibition |
|---|---|---|---|
| 350 | 0 | 25.6 | 0 |
|  | 0.1 | 26.4 | 0 |
|  | 1.0 | 29.7 | 0 |
| 351 | 0 | 43.8 | 0 |
|  | 0.1 | 56.9 | 0 |
|  | 1.0 | 48.4 | 0 |

TABLE 2-continued

Sodium Azide Inhibited Uptake of Peptides with Oct6 NLS

| Peptide | NaN3, % | Geometric MFI | % Inhibition |
|---|---|---|---|
| 352 | 0 | 58.6 | 0 |
|  | 0.1 | 61.8 | 0 |
|  | 1.0 | 47.4 | 19.1 |
| 353 | 0 | 151.4 | 0 |
|  | 0.1 | 155.7 | 0 |
|  | 1.0 | 114.4 | 24.8 |
| 356 | 0 | 417.6 | 0 |
|  | 0.1 | 293 | 29.8 |
|  | 1.0 | 181 | 56.7 |

Legend: DU-145 cells were incubated with 300 nM peptides for 4 hr in the presence or absence of Na azide. Cells were washed and analyzed by flow cytometry to determine the geometric mean fluorescence intensities using a FACScan flow cytometer and CellQuest Pro software. The average of 3 replicate experiments is shown.

However, the geometric MFI of 300 nM peptide 356 was reduced from nearly 418 to 181 in the presence of 1% NaN$_3$, while the geometric MFI of peptide 353 was decreased from 151 to 114 under the same conditions. It was concluded that passage of the smaller peptides was energy-independent but that uptake of the larger peptide containing the Oct6 NLS was an energy-requiring process, and that the effect of temperature on the smaller peptides may have been due to effects on plasma membrane properties. Several mechanisms of peptide uptake are known; ATP-dependent and ATP-independent peptide uptake are two major differentiating features of peptide uptake but by no means the only ones. Even within the same cell line, investigators have observed multiple modes of peptide uptake; endocytic and non-endocytic modes of uptake were noted in the V79 and PC12 cell lines.

Furthermore, the uptake of NLS peptides by the MCF-7 breast cancer cell line was found to be temperature-dependent but unaffected by the presence of NaN$_3$. It was observed that uptake of peptides lacking the Oct6 NLS was temperature-dependent but unaffected by up to 1% NaN$_3$; on the other hand uptake of peptides 353 and 356, both of which contain the Oct6 NLS, was inhibited by 1% NaN$_3$ by over 50% (Table 2). It is concluded from these preliminary studies that uptake of peptides lacking an NLS is likely through a non-endocytic mechanism and is not receptor-mediated whereas uptake of peptide containing an NLS proceed through a different mechanism, but more studies have to be conducting to prove conclusively that this is so.

Peptide 353 Colocalized to the Nucleus.

Figure 3D:
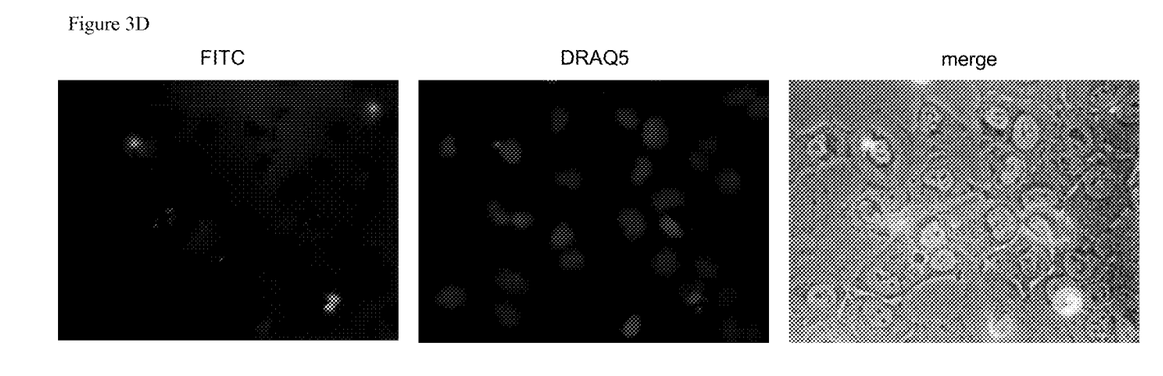

Since flow cytometry only gives data regarding total shifts in fluorescence of a population, imaging flow cytometry and live imaging microscopy studies were performed to determine if the NLS augmented nuclear accumulation of the peptides. Imaging flow cytometry was chosen to provide data on intracellular distribution of FITC-labeled peptides. Inverted epifluorescence microscopy was chosen to eliminate inadvertant artifacts that may arise from fixation, such as nuclear translocation. For these studies, the cell-permeable fluorochrome DRAQ5 was used because it readily enters and stains nuclei of viable cells. Imaging flow cytometry revealed that peptide 353 accumulated in the nucleus of DU-145 and LNCaP cells much better than did peptide 351; at 250 nM it was distributed approximately 50% in the nucleus and 50% in the cytoplasm. It was not retained in the plasma membrane (FIG. 3A). In contrast, peptide 351 showed much less accumulation in the cells when the plasma membrane was excluded from the analysis. To be certain these results were not due to artifactual translocation due to fixation, live cell imaging studies were performed. It was observed that 500 nM of peptide 353, but not peptides 350, 351, or 356, accumulated in the nuclei of DU-145 and LNCaP cells after 24 hrs incubation (FIG. 3B-D). The translocation of peptides to nuclei was complete in the sense that FITC and DRAQ5 fluorescence colocalized in all viable cells, although cytoplasmic fluorescence was visible as well. The FITC distribution was somewhat punctuate in the cytoplasmic portion of cells, leading us to conclude that the peptide may be accumulating within endosomes. It was concluded from these studies that the presence of the EEEAA (SEQ. ID NO. 1) peptide on the N-terminus of the Oct6 NLS enhanced nuclear colocalization as well as uptake.

Peptide 353 Facilitated Transport of a Synthetic Oligonucleotide.

Figure 4:
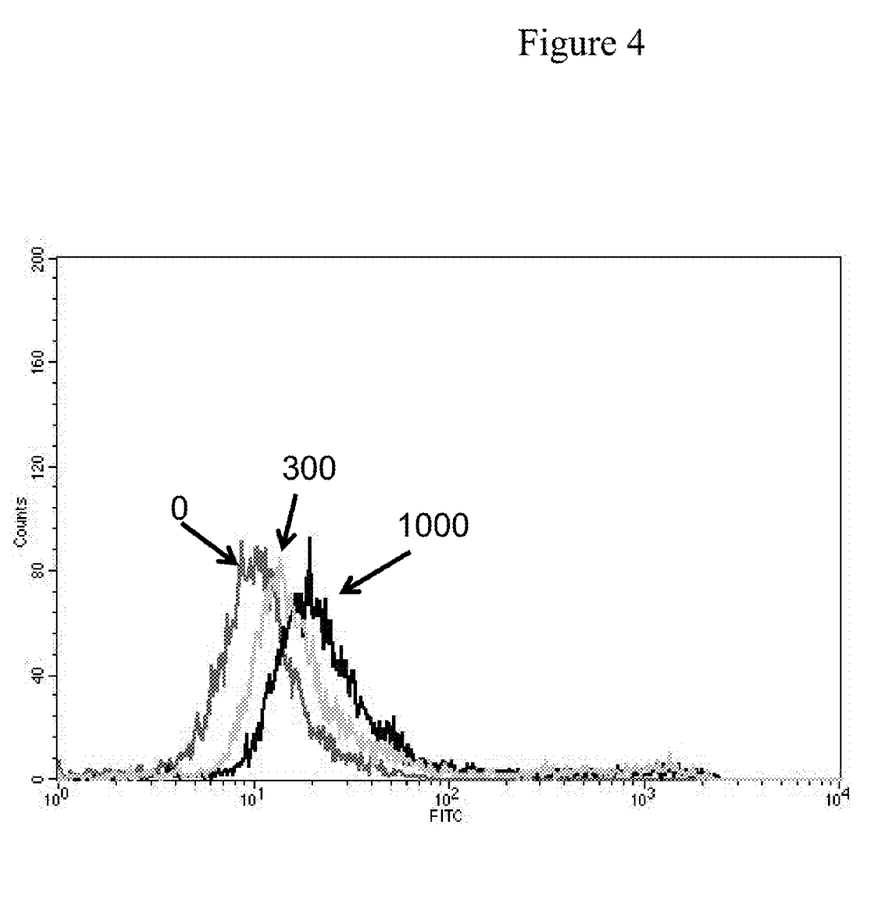
FIG. 4 shows peptide 353 facilitated entry of a PNA into cells. Carboxyfluorescein-labeled 353-PNA at concentrations ranging from 0 to 1000 nM were incubated with DU-145 cells for 18 hr, at which time cells were harvested, washed, and processed for flow cytometry as described previously.

Because the ultimate goal of the studies is to use peptide 353 to ferry in a therapeutic payload cargo, a hybrid molecule 353-PNA was synthesized, which consists of peptide 353 at the N terminus and the carboxyfluorescein peptide nucleic acid (PNA) having the sequence TATGATCTCCTCCGT-lysyl-FITC (SEQ ID NO: 9) at the C terminus. The chemistry of PNA synthesis requires that carboxy terminus FITC be added as lysyl FITC. This PNA has the scrambled sequence of a STAT3-inhibiting oligonucleotide 13778a described previously. Hybrid molecule 353-PNA was incubated with DU-145 cells at 0, 300, and 1000 nM for 18 hr, at which time cells were harvested and processed for flow cytometry. FIG. 4 shows that increasing the concentration of 353-PNA increased the MFI of the cells, and that a small but highly fluorescent population of cells (having MFI greater than 10$^3$) was apparent, even as low as 300 nM. Therefore, peptide 353 facilitated entry of a PNA into DU-145 cells.

Experimental Procedures

Peptides and PNAs: Peptides used are listed in Table 1 and are referred to by their synthesis numbers for convenience. The carboxyfluorescein amino acids were purchased from Bachem. All peptides used had a molar ratio of FITC to peptide of 1. All peptides were synthesized on an Applied Biosystems model 433 peptide synthesizer using FMoc synthesis. After cleavage and deprotection, the peptides were purified by high-performance liquid chromatography (HPLC) and analyzed by both HPLC and matrix-assisted laser desorption/ionization—time-of-flight mass spectroscopy. The peptide-PNA 353-PNA was synthesized by Bio-Synthesis (Lewisville, Tex). It was purified by HPLC and verified by MALDI-TOF. Because of the requirements of PNA chemistry, FITC was added to the C-terminues of 353-PNA as lysyl FITC.

Cells: DU-145 and LNCaP cells were the gift of Dr. James Turkson (University of South Florida, Tampa, Fla.). DU-145 cells were grown in DMEM/Ham's F12 (Invitrogen, Carlsbad, Calif.) plus 10% newborn bovine serum (Hyclone, Logan, Utah). LNCaP cells were maintained in RPMI-1640 (Invitrogen) plus fetal bovine serum (Hyclone). Cell viabilities were determined using fluorescein diacetate (Sigma Chemical Co., St. Louis, Mo.) and a Universal RIII fluorescence microscope (Zeiss, Jena, Germany).

Uptake and Fluorescence Quantification Studies: Peptides were added to subconfluent cultures of cells at times, temperatures, and concentrations indicated in experiments. Concentrations ranging from 0 to 3000 nM were assayed. Cells were analyzed in the presence of 5 mM 7-AAD (eBioscience, San Digeo Calif.) to gate on live events. Fluorescence was quantified, after cells were harvested, using a FACScan flow cytometer. At least 10,000 events were acquired using CellQuest Pro software and an Apple Macintosh G4 dual coprocessor computer running OS X 10.3.9. Fluorescence detectors on the instrument were standardized prior to each acquisition run, so that fluorescence intensities from different days could be compared. Because the FACScan employs logarithmic amplifiers on the fluorescence detectors, the more accurate parameter with which to compare fluorescence intensities for different samples is the geometric mean fluorescence intensity (geometric MFI). In some studies, fixed cells (4% paraformaldehyde/DPBS) were analyzed on an Amnis ImageStream 200 imaging cytometer using IDEAS 3.0 software.

Live Cell Imaging Studies: A Zeiss Axiovert 200 inverted phase-contrast microscope outfitted with epifluorescence was used for live imaging studies. Subconfluent cultures of cells in 12-well plates were incubated with 500 nM peptides as indicated. DRAQ5 (Axxora, San Diego Calif.; 10 mM final concentration) was added for the last hour of incubation, then the cells were washed twice with warm phenol red-free buffer. Cells were examined in phenol red-free buffer plus 10% serum. Images were acquired and analyzed using Zeiss Axiovision software.

Statistical Analysis: The graphing program Kaleidagraph 4.2 (Synergy Software, Reading, Pa.) and the statistical program InStat3 (GraphPad Software, San Diego, Calif.) were used for data analyses unless otherwise indicated.

What is claimed:

1. A cell-penetrating peptide comprising SEQ ID. NO 3.

2. The cell-penetrating peptide of claim 1, further comprising a peptide linker.

3. The cell-penetrating peptide of claim 2, wherein the linker comprises alanine, glycine, or a combination thereof.

4. The cell-penetrating peptide of claim 1, further comprising a nuclear localization signal comprising SEQ. ID NO. 4.

5. The cell-penetrating peptide of claim 4, wherein the cell-penetrating peptide is bound to the N-terminus of the nuclear localization signal.

6. The cell-penetrating peptide of claim 1, further comprising a therapeutic payload.

7. The cell-penetrating peptide of claim 1, further comprising a therapeutic payload wherein the therapeutic payload is bound to the C-terminus of the nuclear localization signal NLS peptide.

8. The cell-penetrating peptide of claim 6, wherein the therapeutic payload comprises a nucleic acid, a liposome, a diagnostic molecule, or a combination thereof.

9. The cell-penetrating peptide of claim 6, further comprising a FITC label.

10. The cell-penetrating peptide of claim 6, wherein the therapeutic payload inhibits the growth of a LN-CaP cell.

11. The cell-penetrating peptide of claim 6, wherein the therapeutic payload comprises a STAT3-inhibiting oligonucleotide.

12. The cell-penetrating peptide of claim 6, wherein the therapeutic payload comprises SEQ ID NO: 9.

13. A composition comprising a cell-penetrating peptide of claim 1 and a STAT3-inhibiting therapeutic payload.

* * * * *